United States Patent [19]

Horiguchi et al.

[11] 4,317,882

[45] Mar. 2, 1982

[54] PRODUCTION OF PLASMINOGEN ACTIVATOR

[75] Inventors: Sadayuki Horiguchi; Akio Hasegawa, both of Fuji; Mitsuru Shibukawa, Yokohama, all of Japan

[73] Assignee: Asahi Kasei Kogyo Kabushiki Kaisha, Osaka, Japan

[21] Appl. No.: 143,680

[22] Filed: Apr. 25, 1980

[30] Foreign Application Priority Data

Apr. 26, 1979 [JP] Japan .................................. 54-50819
Oct. 12, 1979 [JP] Japan ................................. 54-131543

[51] Int. Cl.³ ............................................. C12N 9/48
[52] U.S. Cl. .................................... 435/212; 435/215; 435/240; 435/818
[58] Field of Search ......................... 435/212, 215, 240

[56] References Cited

U.S. PATENT DOCUMENTS 3,873,423 3/1975 Munder ................................... 435/3
3,930,944 1/1976 Nicol ................................... 435/215

Primary Examiner—Lionel M. Shapiro
Attorney, Agent, or Firm—Sughrue, Mion, Zinn, Macpeak and Seas

[57] ABSTRACT

A plasminogen activator having a molecular weight of 45,000 to 68,000 is formed as a single fraction in the cells of human kidney or lung, and is separated and recovered with good efficiency without reducing its molecular weight. The pH of a solution to be contacted with said cells and the concentration of dissolved oxygen should be maintained within suitable ranges in order to form the plasminogen activator having a molecular weight of 45,000 to 68,000 as a single fraction. Furthermore, by properly adjusting the residence time of the solution with the cells, the activator can be formed over a long period of more than 40 days. To separate the activator, the pH of the solution in the separating step is maintained preferably at 4 to 12. By causing a metal chelating agent to be present in the solution in the separating step, the plasminogen activator can be obtained without reducing its molecular weight.

10 Claims, 5 Drawing Figures

PRODUCTION OF PLASMINOGEN ACTIVATOR

BACKGROUND OF THE INVENTION

1. Field of the Invention

This invention relates to a process for producing a plasminogen activator having a molecular weight of 45,000 to 68,000 in a high yield by utilizing cells derived from animals.

2. Description of the Prior Art

Plasminogen activators having a molecular weight of 45,000 to 68,000 are known as useful substances, and isolation of these activators in pure form from human urine has previously been known as a commercial process as described in Japanese Patent Publication No. 10232/1973 and U.S. Pat. No. 4,028,187.

However, the conventional process starting from human urine has several defects; (1) the quality of the raw material is variable, (2) it poses severe hygienic problems, and (3) large quantities of urine of healthy humans are difficult to obtain. In the course of finding a way to overcome such defects, it was noted that cells derived from human beings form plasminogen activators, as reported by E. Barnett and S. Baron *Proc. Soc. Exper. Biol. & Med.*, 102 308 (1959). This method makes it possible to supply raw materials of constant quality in large amounts without a risk of pollution, and a technique of commercializing this method has been desired to be established. However, plasminogen activators formed by cells derived from human beings have a molecular weight of about 30,000, and activators having a molecular weight of about 50,000 can be produced only within a very short initial period after contacting the cells with a plasminogen activator-forming solution, as is reported, for example, in G. H. Barlow, *Thrombosis Research*, Vol. 1, page 201 (1972) and Vol. 11, page 149 (1977).

No method has yet been reported for producing plasminogen activators having a molecular weight of 45,000 to 68,000 in large quantities with good efficiency over a long period of time by utilizing cells derived from human beings.

SUMMARY OF THE INVENTION

As a result of extensive efforts in order to establish a process for commercially producing plasminogen activators having a molecular weight in the range of 45,000 to 68,000, utilizing cells derived from human beings, the process of the present invention has now been attained.

The present invention provides a process for producing a plasminogen activator, which comprises contacting a solution containing a carbon source, a nitrogen source and, if required, inorganic salts, organic additives, or both, with cells derived from human kidneys or lungs and having the ability to produce a plasminogen activator and then separating the resulting plasminogen activator from the solution. This contacting is carried out while maintaining the pH of the solution at from about 6 to 9 and the concentration of dissolved oxygen therein at a level of at least 30% of the saturation concentration of dissolved oxygen, followed by treating the resulting solution at a pH of from about 4 to 12, to thereby separate and recover a plasminogen activator having a molecular weight of 45,000 to 68,000.

DETAILED DESCRIPTION OF THE INVENTION

Figure 1:
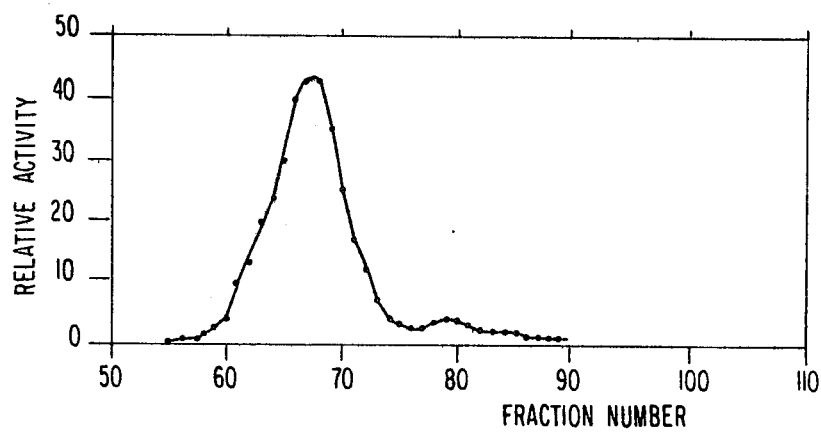
FIG. 1 shows a gel filtration distribution pattern of a plasminogen activator formed according to the invention using kidney cells.

The cells used in the process of this invention are derived from human kidneys or lungs and have the ability to produce plasminogen activators. These cells can be grown by cultivating methods usually employed in the cultivation of animal cells, for example, by the method described in a Japanese-language publication *Tissue Culture*, pages 3–38 (edited by Jyunnosuke Nakai et al., published in 1976 by Asakura Shoten).

Any solution conventionally employed for the production of plasminogen activators using cells derived from animals can be used as the solution to be contacted with the cells for forming plasminogen activators according to the process of the present invention. Such solutions are, for example, described in *Proc. Soc. Exper. Biol. & Med.* 102 308 (1959), *J. Lab. & Clim. Med.* 70 650 (1967), *J. Clin. Inv.* 47 1238 (1968) and *J. Clin. Inv.* 48 1740 (1969).

As carbon sources that can be included in this solution, sugars, i.e. sucrose, maltose and glucose, can be used.

Organic nitrogen sources are suitable as nitrogen sources, with amino acid mixtures and hydrolyzates of proteins being preferred. The proteins may be of animal or vegetable origin; hydrolyzates of casein, soybean protein, lactoalbumin and animal flesh proteins give good results, and are generally preferred.

In addition to nitrogen and carbon sources, inorganic salts, organic additives, or both, may be added, if required, to obtain constant results, and it is particularly preferred that these materials are added when amino acid mixtures are used as the nitrogen sources. Examples of the inorganic salts are $NaCl$, $KCl$, $MgCl_2$, $MgSO_4$, $NaH_2PO_4$, $Na_2HPO_4$, $KH_2PO_4$, $CuSO_4$, $Fe(NO_3)_3$, $FeSO_4$, $MnCl_2$, $(NH_4)_2MoO_4$, $ZnSO_4$ and the like. Examples of the organic additives are p-aminobenzoic acid, ascorbic acid, D-biotin, calciferol, calcium D-panthotenate, cholesterol, choline chloride, folic acid, i-inositol, menadion, nicotinamide, nicotinic acid, pyridoxal, pyridoxine, riboflavin, thiamine, DL-α-tocopherol, Tween 80, vitamin A, adenine, AMP, ATP, deoxyribose, rebose, glutathione, guanine, hypoxanthine, thymine, uracil, xanthine, sodium acetate and the like.

Organic acids are also examples of additives preferably added to the nutrient source. Succinic acid, malic acid, fumaric acid and glycolic acid are preferred. Fumaric acid is particularly preferred. Instead of, or together with, these organic acids, serine, threonine and glycine may be added.

By contacting the solution with the cells while maintaining the pH of the solution at from about 6 to 9 (and preferably from 7 to 8), its temperature at from about 15° to 45° C. (and preferably at 25° to 40° C.), and the concentration is dissolved oxygen at a level of at least 30% of the saturation concentration of oxygen, plasminogen activator having a molecular weight in the range of 45,000 to 68,000 (measured by a gel filtration method) can be produced. In particular, by adjusting the residence time of the solution with the cells to not more than 30 days (i.e., by changing the solution within 30 days), plasminogen activators containing at least 95% of the fraction having a molecular weight in the range of 45,000 to 68,000 can be produced over more than 60 days. Preferably, by adjusting the residence time to not more than 10 days (i.e., by changing the solution within 10 days), a plasminogen activator having a molecular weight in the range of 45,000 to 68,000 can be produced as a single fraction in great quantities over more than 40 days. The term "residence time" used herein means the period of time in which the solution is periodically changed. Changing of the solution may be performed continuously or discontinuously.

The solution obtained has a low concentration of the plasminogen activator, and contains many impurities. Therefore, it is necessary to separate the activator from the solution to obtain it in a high concentration and in a highly pure form. Many methods are known by which such a separation can be achieved, as described in, for example, *Biochemistry* 5 2160 (1966), *J. Biol. Chem.* 249 4295 (1974) and *Methods in Enzymology* 35 451 (1974), such as: a salting out method using ammonium sulfate, sodium chloride, sodium sulfate, ammonium chloride, and so forth; a dialyzing method: an adsorption method using silica gel, hydroxyappatite, barium sulfate, an acrylonitrile-methyl acrylate copolymer, and so forth; an ion-exchange chromatographic method using carboxymethyl dextran, phosphocellulose, and so forth; a gel filtration method using acrylamide gel, agarose, crosslinked dextran gel, and so forth; an affinity chromatographic method using lysine-agarose, benzamidine-agarose, para-aminobenzamidine-agarose, arginine ester-agarose, and so forth; a preparative disc electrophoretic method using polyacrylamide gel; and an isoelectric electrophoretic method using an amphoteric carrier. These methods may be used singly or in combination with each other.

For the purpose of the present invention, the separation of the plasminogen activator from the solution is preferably performed while maintaining the pH of the solution at 4 to 12.

It has also been found that in the step of separating the resulting plasminogen activator by these methods, either singly or in combination, the presence of a metal chelating agent in the solution makes it possible to reduce decomposition or denaturation during separation, to give a highly pure plasminogen activator with a molecular weight in the range of 45,000 to 68,000 in a high recovery ratio, as will be seen in the Examples described hereinbelow.

Examples of the metal chelating agent that can be used for this purpose include ammonium N-nitrosophenyl hydroxylamine, ammonium purpurate, α-benzoin oxime, 2,3-butanedione dioxime, trans-1,2-diaminocyclohexanetetraacetic acid, 4,5-dihydroxybenzene-1,3-disulfonic acid, 2,3-dimercapto-1-propanol, diphenyl thiocarbazone, 2,2'-dipyridyl, 3,6-disulfo-1,8-dihydroxynaphthalene, dithiooxamide, Eriochromeschwarz T, ethylene glycol (2-aminoethyl ether)-N',N'-tetraacetic acid, ethylenediamine, ethylenediaminetetraacetic acid, ortho-hydroxybenzaldehyde oxime, salicylic acid, 8-hydroxyquinoline, 8-hydroxyquinoline-sulfonic acid, 4-methyl-1,2-dimercaptobenzene, 5-nitro-1,10-phenanthroline, ortho-phenanethroline, potassium ethyl xanthate, diethyl dithiocarbamyl sodium salt, 2-thenoyl-2-furoylmethane, thenoyltrifluoroacetone, and thiourea.

These metal chelating agents can be used either singly or as mixtures of two or more thereof. Of these, ethylenediaminetetraacetic acid, trans-1,2-diaminocyclohexanetetraacetic acid, and ortho-phenanthroline give particularly favorable results. A suitable concentration of the metal chelating agent in the solution is at least 0.1 millimole, preferably at least 0.3 millimole, per liter of the solution. There is no particular upper limit concerning the concentration of the metal chelating agent, but in practice, up to 5 millimole of the metal chelating agent can be added.

The process of this invention is free from the defects of the prior art, i.e. low concentration of the starting urine, the difficulty of collecting large amounts of urine of stable quality from healthy humans, the existence of hygienic problems in the handling of urine, and the low molecular weight of the recovered plasminogen activators. It is suitable as a commercial process for producing plasminogen activators having a molecular weight of 45,000 to 68,000, of stable quality, high purity, and in high concentrations with a high recovery ratio.

As is reported by OLS No. 2,815,853 and *Medicine & Drug Journal* 14 233–237 (1978), plasminogen activators having a molecular weight in the range of from 45,000 to 68,000 as obtained by the process of this invention have higher activity than those having a molecular weight outside the range. Further the plasminogen activators obtained by this process have a uniform molecular weight, and therefore, can be standardized as a substance. Accordingly, it is easy to standardize their efficacy as medicines, and to accurately predict their effect upon administration.

The following Examples illustrate the invention in more detail.

Figure 2:
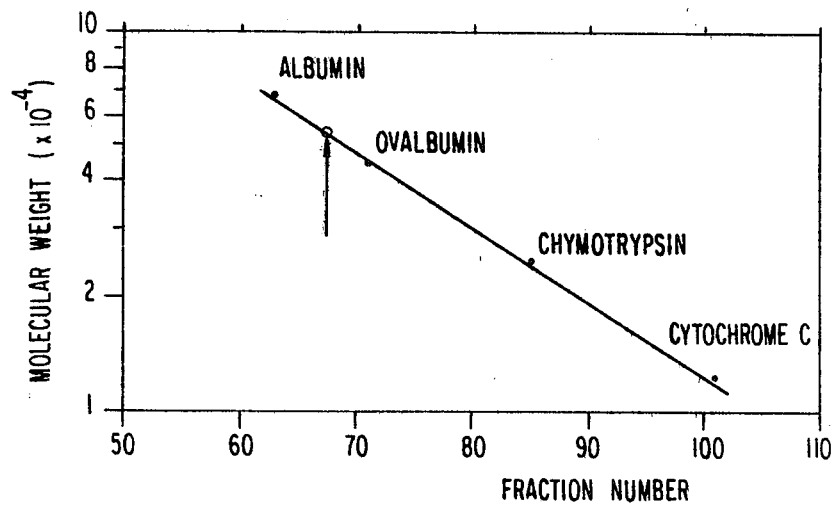
FIG. 2 shows the relationship between the molecular weights of plasminogen activator formed according to the invention using kidney cells and standard proteins, with respect to the eluted fraction numbers of the gel filtration of FIG. 1.
Figure 3:
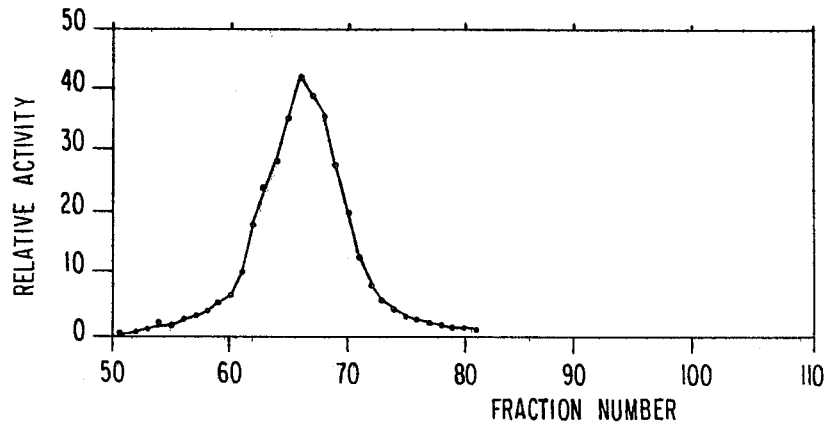
FIG. 3 shows a gel filtration distribution pattern analogous to FIG. 1 except formed using lung cells.
Figure 4:
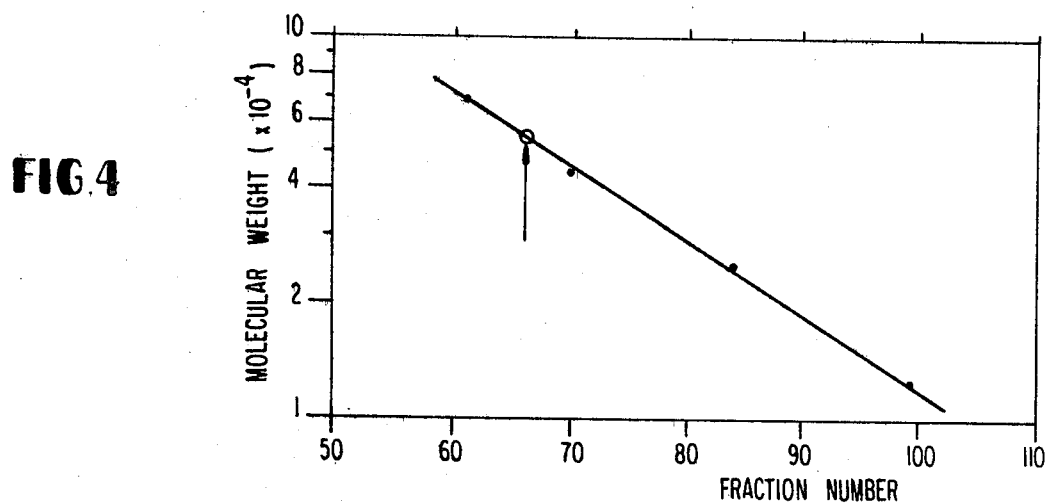
FIG. 4 is a diagram analogous to FIG. 2, showing the relationship between the molecular weights of plasminogen activator formed according to the invention using lung cells and standard proteins.
Figure 5:
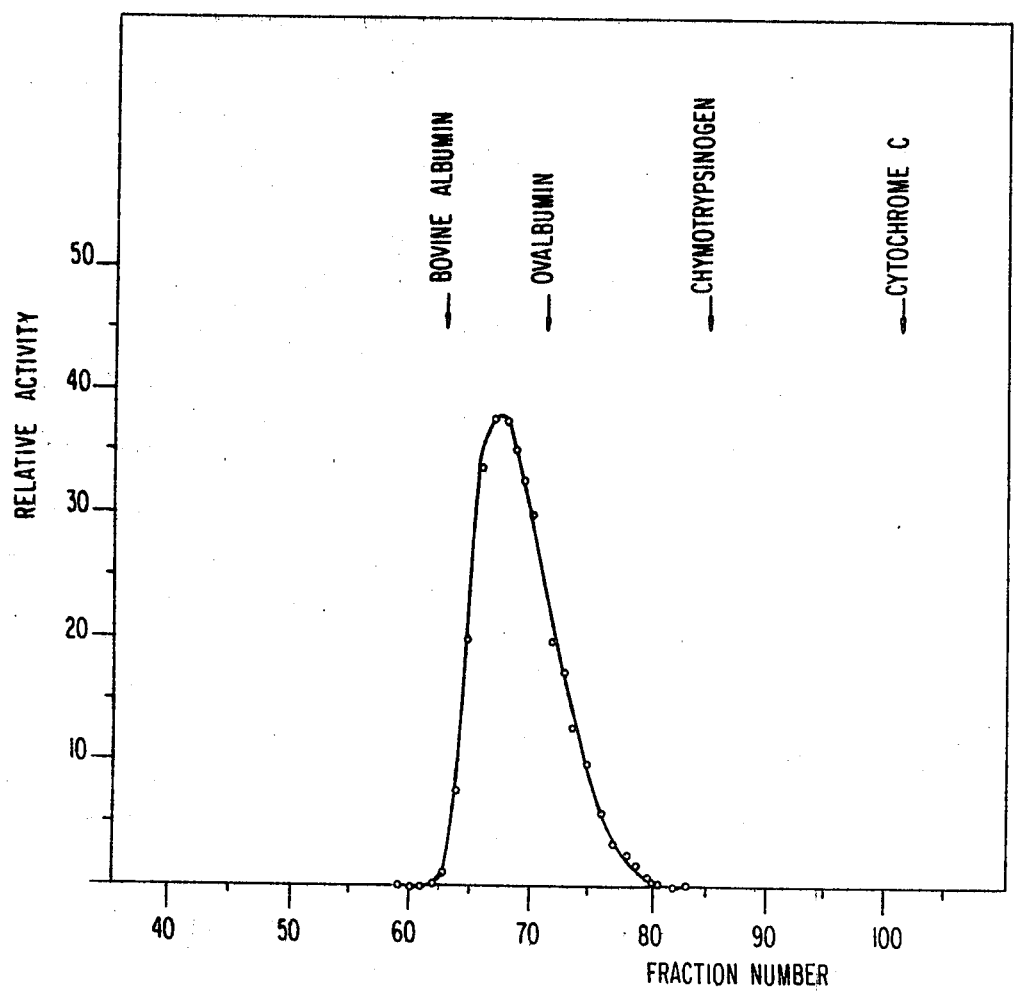
FIG. 5 is a gel filtration distribution pattern, obtained using Sephadex G100, for plasminogen activator obtained according to Example 1.

The drawings referred to in these Examples are as follows:

FIG. 1 shows a gel filtration distribution pattern of a plasminogen activator formed using kidney cells, wherein the abscissa representing fraction numbers and the ordinate representing the activity of the enzyme;

FIG. 2 is a diagram showing the relation between the molecular weights of standard proteins and eluted fraction numbers in gel filtration, the arrow showing the site of the maximum elution of a plasminogen activator formed using kidney cells as shown in FIG. 1;

FIG. 3 shows a gel filtration distribution pattern of a plasminogen activator formed using lung cells, the abscissa and the ordinate representing the same items as in FIG. 1;

FIG. 4 is a chart similar to FIG. 2, the arrow showing the site of maximum elution of a plasminogen activator formed using lung cells as in FIG. 3; and FIG. 5 is a gel filtration distribution pattern obtained using Sephadex G100 of the plasminogen activator obtained by the method of Example 7, the abscissa representing fraction numbers, the ordinate representing the relative activity of the enzyme, and the arrow showing the site of elution of standard proteins.

EXAMPLE 1

A solution having the composition shown in Table 1 was fed to fully grown human kidney cells (obtained from Flow Laboratories) from a reservoir in an amount of 20 ml per 100,000 cells, and maintained at 37° C. The solution of the reservoir was maintained at pH 7.5 with sodium hydroxide during the reaction. The concentration of dissolved oxygen in the solution was maintained at a level of at least 50% of the saturated concentration of dissolved oxygen. After 40 days, the solution was recovered, and the concentration of plasminogen activator was measured and found to be 70 IU/ml. The solution was dialyzed against tris-HCl buffer at a pH of 7.8 and examined for molecular weight by a gel filtration method using Sephadex G100 (a bead-formed crosslinked dextran gel, sold by Pharmacia Co.). As standard proteins, albumin (M.W. 68,000), ovalbumin (M.W. 45,000), Chymotrypsin (M.W. 25,000), and cytochrome (M.W. 12,500) were used. As shown in FIGS. 1 and 2, more than 95% of the resulting plasminogen activator had a peak of molecular weight within the range of from 45,000 to 68,000.

TABLE 1

| | mg/L |
|---|---|
| Amino acids | |
| L-arginine hydrochloride | 21.1 |
| L-cystine | 12.0 |
| L-glutamine | 292.0 |
| L-histidine hydrochloride monohydrate | 10.5 |
| L-isoleucine | 26.2 |
| L-leucine | 26.2 |
| L-lysine hydrochloride | 36.5 |
| L-methionine | 7.5 |
| L-phenylalanine | 16.5 |
| L-threonine | 23.8 |
| L-tryptophane | 4.0 |
| L-tyrosine | 18.1 |
| L-valine | 23.4 |
| Vitamins | |
| D-biotin | 1.0 |
| D-Ca-panthothenic acid | 1.0 |
| Choline chloride | 1.0 |
| Folic acid | 1.0 |
| i-Inositol | 1.8 |
| Nicotinamide | 1.0 |
| Pyridoxal hydrochloride | 1.0 |
| Riboflavin | 0.1 |
| Thiamine hydrochloride | 1.0 |
| Inorganic salts | |
| NaCl | 8000.0 |
| KCl | 400.0 |
| $Na_2HPO_4 \cdot 2H_2O$ | 60.0 |
| $KH_2PO_4$ | 60.0 |
| $MgSO_4 \cdot 7H_2O$ | 100.0 |
| $CaCl_2$ (anhydrous) | 140.0 |
| $MgCl_2 \cdot 6H_2O$ | 100.0 |
| Other additives | |
| Glucose | 1000.0 |
| Lactoalbumin hydrolyzate | 5000.0 |
| Disodium fumarate | 5000.0 |

EXAMPLE 2

A solution having the composition shown in Table 1 was applied to fully grown human lung cells (obtained from Flow Laboratories) as in Example 1, and maintained at 37° C. for 30 days, at a pH 7.3 to 7.7. The concentration of dissolved oxygen in the solution was maintained at a level of at least 50% of the saturated concentration of the dissolved oxygen. After 30 days, the solution was recovered, and dialyzed against tris-HCl buffer having a pH of 7.8, and then analyzed for molecular weight by gel filtration on Sephadex G-100 (Pharmacia Co.). As shown in FIGS. 3 and 4, the resulting plasminogen activator showed a peak of molecular weight within the range from 45,000 to 68,000.

EXAMPLE 3

A solution having the composition shown in Table 3 below were supplied from a reservoir to five containers containing fully grown human kidney cells (Flow Laboratories) in an amount of 20 ml per 100,000 cells, and they were maintained at 37° C., with the solution supplied having pH's of 5, 6, 7, 8 and 9, respectively, adjusted by a solution of hydrochloric acid or sodium hydroxide. The concentration of dissolved oxygen in each of the solution was maintained at 50% of the saturated concentration of dissolved oxygen. After 40 days, the solutions were recovered, dialyzed against a phosphate buffer having a pH of 7.4, and developed on a column of CM Sephadex C-50 (Pharmacia Co.) using a 0.1 M phosphate buffer containing 0 to 0.5 M sodium chloride. Plasminogen activator in which the individual active fractions had a molecular weight in the range of 45,000 to 68,000 was detected by gel filtration, and the results for various pH values are shown in Table 2.

The desired activator was most desirably obtained when the solution was maintained at a pH of at least 6.

TABLE 2

| pH | 5 | 6 | 7 | 8 | 9 |
|---|---|---|---|---|---|
| Plasminogen activator | − | + | +++ | +++ | +++ |

−: None (Not detected)
+: Very small amount
++: Small amount
+++: Great amount

TABLE 3

| | mg/L |
|---|---|
| Amino acids | |
| L-alanine | 25.0 |
| L-arginine hydrochloride | 70.0 |
| L-aspartic acid | 30.0 |
| L-cysteine hydrochloride | 0.1 |
| L-cystine | 20.0 |
| L-glutamic acid | 67.0 |
| L-glutamine | 100.0 |
| L-glycine | 50.0 |
| L-histidine hydrochloride monohydrate | 22.0 |
| L-hydroxyproline | 10.0 |
| L-isoleucine | 20.0 |
| L-leucine | 60.0 |
| L-lysine hydrochloride | 70.0 |
| L-methionine | 15.0 |
| L-phenylalanine | 25.0 |
| L-proline | 40.0 |
| L-tryptophan | 10.0 |
| L-tyrosine | 40.0 |
| L-valine | 25.0 |
| L-serine | 25.0 |
| L-threonine | 30.0 |
| Inorganic salts | |
| $Fe(NO_3)_3 \cdot 9H_2O$ | 0.70 |
| NaCl | 8000.0 |
| KCl | 400.0 |
| $Na_2HPO_4 \cdot 2H_2O$ | 60.0 |
| $KH_2PO_4$ | 60.0 |
| $MgSO_4 \cdot 7H_2O$ | 100.0 |
| $CaCl_2$ (anhydrous) | 140.0 |
| $MgCl_2 \cdot 6H_2O$ | 100.0 |
| Others | |
| Glucose | 1000.0 |

TABLE 3-continued

| | mg/L |
|---|---|
| Disodium fumarate | 5000.0 |

EXAMPLE 4

A solution having the composition shown in Table 3 was fed from a reservoir to four containers containing fully grown human kidney cells (Flow Laboratories) in an amount of 20 ml per 100,000 cells, and they were maintained at 37° C. The solutions fed to the individual solutions were adjusted to a dissolved oxygen concentration of 10, 15, 30, 60, and 90% respectively of saturation using nitrogen, oxygen and air, and also at a pH of 7.3. After a lapse of 40 days, each of the solutions was recovered, and dialyzed against tris-HCl buffer having a pH of 7.8, and a plasminogen activator having a molecular weight of 45,000 to 68,000 was detected. As shown in Table 4, the desired activator was detected by maintaining the dissolved oxygen concentration at a level of at least 15% of saturation. The marked formation of the activator was noted at a dissolved oxygen concentration of at least 30% of saturation.

TABLE 4

| Dissolved oxygen (%) | 10 | 15 | 30 | 60 | 90 |
|---|---|---|---|---|---|
| Plasminogen activator | + | ++ | +++ | +++ | +++ |

EXAMPLE 5

A solution having the composition shown in Table 3 was applied to fully grown human kidney cells (Flow Laboratories) in an amount of 20 ml per 100,000 cells and maintained at 37° C. The solution was maintained at a pH of 7.3 and a dissolved oxygen concentration of at least 60% of saturation. After 40 days, the solution was recovered, and dialyzed against a citrate buffer having a pH of 3 and 4 (Data For *Biochemical Research* 2nd ed. page 486, 1969), a sodium acetate buffer having a pH of 5 (ibid, page 487), a phosphate buffer having a pH of 6 and 7 (ibid, page 489), a tris-HCl buffer having a pH of 8 and 9 (ibid, page 494), a borate buffer having a pH of 10 (ibid, page 497) and a sodium phosphate buffer having a pH of 11 and 12 (ibid, page 498), and then a measurement for plasminogen activator having a molecular weight of 45,000 to 68,000 was made. The results are shown in Table 5.

TABLE 5

| pH of post-treatment for separation of the activator | 3 | 4 | 5 | 6 | 7 | 8 | 9 | 10 | 11 | 12 |
|---|---|---|---|---|---|---|---|---|---|---|
| Plasminogen activator | − | + | ++ | +++ | +++ | +++ | +++ | +++ | ++ | ++ |

The desired activator was detected when the post-treatment was carried out at a pH of at least 4.

EXAMPLE 6

A solution having the composition shown in Table 3 was applied to fully grown human kidney cells (Flow Laboratories) in an amount of 0.4 ml per 100,000 cells and maintained at 37° C. The solution was maintained at a pH of 7.3 and a dissolved oxygen concentration of at least 60% of saturation. The solution was wholly changed every 10, 20 and 30 days respectively in three separate containers, and the solution was contacted with the cells for a total of 60 days in each container. The solutions recovered upon exchange were dialyzed against a tris-HCl buffer having a pH of 7.8, and analyzed for molecular weight by gel filtration. The results are shown in Table 6. When the residence time of the solution with the cells was 10 days (that is, the solution was changed every 10 days), 98 to 100% of plasminogen activator having a molecular weight in the range of 45,000 to 68,000 was detected. When the residence time was 30 days, at least 95% of plasminogen activator having a molecular weight in the range of 45,000 to 68,000 was detected.

TABLE 6

| Residence time (days) | Solution changing | Molecular weight 45,000-68,000 | Others |
|---|---|---|---|
| 10 | 1 | 100% | 0% |
|  | 2 | 100 | 0 |
|  | 3 | 100 | 0 |
|  | 4 | 100 | 0 |
|  | 5 | 99 | 1 |
|  | 6 | 98 | 2 |
| 20 | 1 | 100 | 0 |
|  | 2 | 99 | 1 |
|  | 3 | 97 | 3 |
| 30 | 1 | 97 | 3 |
|  | 2 | 95 | 5 |

EXAMPLE 7

A solution having the composition shown in Table 1 was applied to fully grown human kidney cells (Flow Laboratories) in an amount of 0.4 ml per 100,000 cells and maintained at 37° C. The solution was maintained at a pH of 7.3 and a dissolved oxygen concentration of at least 50% of saturation. The solution was wholly changed every 7 days, and the cells were contacted with the solution for a total period of 49 days. The solution was recovered, and its content of a plasminogen activator was measured by a fibrin plate method (Arch. Biochem. Biophys. 40 346 (1952)) was found to be 628 CTA units/ml. It consisted of a single fraction having a molecular weight of 45,000 to 68,000. Ammonium sulfate was added to 250 ml of the solution to a concentration of 70% of saturation. The precipitate was recovered by centrifugal separation, and dialyzed at 4° C. for 48 hours against a 10 mM phosphate buffer having a pH of 7.0 and containing 1 mM ethylenediamine tetraacetic acid. The enzyme solution was subsequently absorbed to a column of CM Sephadex C50 (Pharmacia Co.) equilibrated with a 10 mM phosphate buffer having a pH of 7.0 and containing 1 mM ethylene diaminetetraacetic acid, and eluted with a 10 mM phosphate buffer having a pH of 7.0 and containing 0.3 M sodium chloride and 1 mM ethylenediaminetetraacetic acid. The solution was further concentrated, and purified by gel filtration using a 50 mM phosphate buffer having a pH of 7.0 and containing 0.5 M sodium chloride and 1 mM ethylenediamine as a developing solvent. The amount of the plasminogen activator recovered by the above procedure was 87900 CTA units, and the ratio of recovery was 56%. The molecular weight of the plasminogen activator was measured by gel filtration of Sephadex G-100 using cytochrome C, chymotripsionogen, oval- bumin and bovine albumin for molecular weight markers. As is shown in FIG. 5, plasminogen activator having a molecular weight in the range of 45,000 to 68,000 was obtained as a single fraction.

250 ml of the starting solution containing the same plasminogen activator as above was purified under the same conditions as above except that the solution used in post-treatment did not contain ethylenediaminetetraacetic acid. The amount of the plasminogen activator recovered was 36100 CTA units, and the recovery ratio was 23%.

EXAMPLE 8

A solution of the composition shown in Table 1 was applied to fully grown human lung cells (Flow Laboratories) in an amount of 0.4 ml per 100,000 cells and maintained at 37° C. The solution was maintained at a pH of 7.3, and a dissolved oxygen concentration of at least 52% of saturation. The solution was wholly changed every 7 days, and the cells were contacted with the solution for a total of 42 days. The solution was recovered, and its content of plasminogen activator was measured and found to be 158 CTA units/ml. It consisted of a single fraction having a molecular weight of 45,000 to 68,000.

200 ml of the resulting crude enzyme solution was fractionated with ammonium sulfate in the same way as in Example 7. The precipitate obtained was dialyzed at 4° C. for 48 hours against a 10 mM citrate buffer having a pH of 6.0 and containing 1 mM trans-1,2-diaminocyclohexanetetraacetic acid, then adsorbed to phosphocellulose equilibrated with the same buffer as above, and then eluted with a solution prepared by adding 0.3 M sodium chloride to the same buffer as above. The solution was further concentrated, and purified by gel filtration on Sephadex G100 using 0.05 M tris-HCl buffer having a pH of 8.0 and containing 0.5 M sodium chloride and 1 mM trans-1,2-diaminocyclohexanetetraacetic acid. The amount of the resulting plasminogen activator was 15200 CTA units, and the ratio of recovery was 48%. When the molecular weight of this product was measured by the same gel filtration method as in Example 7, a plasminogen activator as a single fraction having a molecular weight in the range of 45,000 to 68,000 was obtained.

200 ml of the starting solution containing the same plasminogen activator as above was purified under the same conditions as above except that the solution used in post-treatment did not contain trans-1,2-diaminocyclohexanetetraacetic acid. The amount of the plasminogen activator recovered was 5690 CTA units, and the ratio of recovery was 18%.

EXAMPLE 9

By the same procedure as in Example 7, a solution containing 680 CTA units/ml of a plasminogen activator was obtained. To 200 ml of the solution was added 3 g of an acrylonitrile-methyl acrylate copolymer, and the mixture was stirred for 1 hour to cause adsorption of the plasminogen activator thereto. It was collected by filtration, washed with water, and eluted at a low temperature with 50 ml of 4% aqueous ammonia containing 1 mM of ortho-phenanthroline. The solution was subsequently dialyzed for 48 hours against a 10 mM phosphate buffer having a pH of 7.0 and containing 1 mM ortho-phenanthroline, adsorbed to hydroxyappatite equilibrated with the same buffer as above, and eluted while continuously replacing it with a 0.4 M phosphate buffer having a pH of 7.0 and containing 1 mM ortho-phenanethroline. Fractions having plasminogen activity were recovered, and subjected to gel filtration on Sephadex G100 using a 0.05 M phosphate buffer having a pH of 7.0 and containing 1 mM ortho-phenanthroline and 0.5 M sodium chloride as a developing solvent. The plasminogen activator was further adsorbed to para-aminobenzamidine-agarose equilibrated with a 0.05 M phosphate buffer having a pH of 7.0 and containing 1 mM ortho-phenanthroline and 0.5 M sodium chloride, and eluted with a 0.1 M acetate buffer having a pH of 4.0 and containing 1 mM ortho-phenanthroline and 1 M sodium chloride. The total activity of the resulting plasminogen activators was 42400 CTA units, and the ratio of recovery was 31%. This product showed a single band in disc electrophoresic and sodium dodecylsulfate polyacrylamide gel electrophoresis. When its molecular weight was measured by sodium dodecylsulfate polyacrylamide gel electrophoresis using bovine albumin, ovalbumin, chymotrypsinogen and cytochrome C as standard proteins, only a single protein having a molecular weight in the range of 45,000 to 68,000 was detected.

When the same post-treatment as above was performed using 200 ml of the starting solution containing the same plasminogen activator under the same conditions as above except that the solution used in post-treatment did not contain ortho-phenanthroline, the total activity of the recovered plasminogen activators was 19000 CTA units, and the ratio of recovery was 14%.

COMPARATIVE EXAMPLE 1

Fully grown whole human embryo cell (Flow Laboratories) were treated in the same way as in Example 7 to afford a solution containing 97 CTA units/ml of a plasminogen activator. This plasminogen activator consisted of a single fraction having a molecular weight of 45,000 to 68,000. 100 ml of this solution was fractionated with ammonium sulfate in the same way as in Example 7. The precipitate was dialyzed at 4° C. for 48 hours against a 10 mM phosphate buffer having a pH of 7.0 and containing 1 mM ethylenediaminetetraacetic acid. After the dialysis, the total activity was 4750 CTA units, and the percent residue was 49%.

Separately, a precipitate was obtained from 100 ml of the same solution as above, and dialyzed against a buffer not containing ethylenediaminetetraacetic acid. The residual activity was 52%.

The solution after dialysis in the present Comparative Example 1 contained 60 to 62% of a plasminogen activator fraction having a molecular weight in the range of about 30,000. It was impossible to recover plasminogen activator having a molecular weight of 45,000 to 68,000 as a single fraction without reducing its molecular weight.

EXAMPLE 10

For comparison, the solution obtained in Example 7 was treated in the same way as in Comparative Example 1. The residual activity was 99%, and 42%, respectively.

The resulting plasminogen activators all had a molecular weight of 45,000 to 68,000, and did not contain a fraction having a molecular weight in the range of about 30,000.

Specifically, it was found that the addition of a metal chelating agent is effective for obtaining a plasminogen activator from a solution produced by cells derived from kidneys or lungs. With respect to the whole embryo cells, the metal chelating agent did not inhibit decomposition, denaturation and deactivation of the plasminogen activator.

EXAMPLE 11

A solution containing a plasminogen activator obtained by the same method as in Example 7 was fractionated with ammonium sulfate in the same way as in Example 7. The precipitate was dialyzed for 48 hours against 10 mM phosphate buffer having a pH of 7.0 and containing ortho-phenanthroline trans-1,2-diaminocyclohexanetetraacetic acid, or ethylenediaminetetraacetic acid in the various concentrations shown in Table 7. The results are also shown in Table 7.

TABLE 7

| Amount added (mM) | Residual activity (%) | | |
|---|---|---|---|
| | o-Phenan-throline | Trans-1,2-diamino-cyclohexanetetra-acetic acid | Ethylenediamine-tetraacetic acid |
| 0 | 50 | 40 | 45 |
| 0.05 | 61 | 63 | 68 |
| 0.1 | 81 | 82 | 85 |
| 0.3 | 97 | 95 | 96 |
| 0.5 | 98 | 97 | 99 |
| 1.0 | 95 | 97 | 97 |
| 3.0 | 92 | 92 | 92 |
| 5.0 | 90 | 93 | 91 |

A marked effect was observed when the amount added was at least 0.1 mM, and the plasminogen activator was almost quantitatively recovered when the amount added was at least 0.3 mM.

In an amount of at least 0.1 mM, at least 95% of the recovered plasminogen activator had a molecular weight in the range of 45,000 to 68,000. Particularly, when the amount was at least 0.3 mM, the fraction having a molecular weight in the range of 45,000 to 68,000 was obtained almost 100%.

EXAMPLE 12

The same procedures as in Example 1 were repeated except that sucrose or maltose was used as the carbon source in place of glucose in the solution to be contacted with the cells. As a result, more than 95% of the resulting plasminogen activator had a peak of molecular weight within the range of from 45,000 to 68,000.

While the invention has been described in detail and with reference to specific embodiments thereof, it will be apparent to one skilled in the art that various changes and modifications can be made therein without departing from the spirit and scope thereof.

What we claim is:

1. A process for producing plasminogen activator having a molecular weight in the range from about 45,000 to 68,000, which comprises:
   (1) contacting a solution containing a carbon source and a nitrogen source with cells derived from human kidneys or lungs and having the ability to produce a plasminogen activator while maintaining the pH of said solution in a range from about 6 to 9 and the concentration of dissolved oxygen in said solution at a level of at least 30% of the saturation concentration of dissolved oxygen; and
   (2) separating the resulting plasminogen activator from the solution while maintaining the pH in a range from about 4 to 12.

2. A process as in claim 1, wherein by adjusting the residence time of solution with the cells to not more than 30 days, at least 95% of the plasminogen activator formed over a period of at least 60 days has a molecular weight in the range of 45,000 to 68,000.

3. A process as in claim 1, wherein by adjusting the residence time of solution with the cells to not more than 10 days, the plasminogen activator formed over a period of at least 40 days has a molecular weight in the range of 45,000 to 68,000 as a single fraction.

4. A process as in claim 1, 2 or 3, wherein step (2) is carried out in the presence of at least one metal chelating agent.

5. The process of claim 4, wherein the concentration of said metal chelating agent in the solution is at least 0.1 millimole per liter of the solution.

6. The process of claim 4, wherein the concentration of said metal chelating agent in the solution is at least 0.3 millimole per liter of the solution.

7. A process as in claim 4, wherein said chelating agent is at least one member selected from the group consisting of ortho-phenanthroline, trans-1,2-diaminocyclohexanetetraacetic acid and ethylenediaminetetraacetic acid.

8. A process as in claim 5, wherein said chelating agent is at least one member selected from the group consisting of ortho-phenanthroline, trans-1,2-diaminocyclohexanetetraacetic acid and ethylenediaminetetraacetic acid.

9. A process as in claim 6, wherein said chelating agent is at least one member selected from the group consisting of ortho-phenanthroline, trans-1,2-diaminocyclohexanetetraacetic acid and ethylenediaminetetraacetic acid.

10. A process as in claim 1, 2 or 3, wherein step (1) is carried out at a temperature of from about 15° to 45° C.

* * * * *